United States Patent
Haarer et al.

(10) Patent No.: US 6,482,192 B2
(45) Date of Patent: Nov. 19, 2002

(54) DISCRETE ABSORBENT ARTICLES

(75) Inventors: Jutta S. Haarer, Princeton, NJ (US); Joseph M. Luizzi, Newtown; H. Michael Moscherosch, Doylestown, both of PA (US); Miriam O. Motta, Franklin Park, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/971,454

(22) Filed: Oct. 5, 2001

(65) Prior Publication Data

US 2002/0115975 A1 Aug. 22, 2002

Related U.S. Application Data

(63) Continuation-in-part of application No. 09/740,337, filed on Dec. 19, 2000.

(51) Int. Cl.7 .................................................. A61F 13/15
(52) U.S. Cl. .................................. 604/385.01; 604/358
(58) Field of Search ................................ 604/317–355, 604/356–402; 2/400–406

(56) References Cited

U.S. PATENT DOCUMENTS

| | | | | |
|---|---|---|---|---|
| 4,444,193 A | * | 4/1984 | Fogt et al. | 128/632 |
| 4,556,056 A | * | 12/1985 | Fischer et al. | 128/156 |
| 4,789,211 A | * | 12/1988 | Wreede | 350/3.61 |
| 4,917,112 A | * | 4/1990 | Kalt | 128/156 |
| 5,106,362 A | * | 4/1992 | Gilman | 602/47 |
| 5,462,538 A | | 10/1995 | Korpman | |
| 5,681,305 A | | 10/1997 | Korpman | |
| 5,738,641 A | * | 4/1998 | Watson et al. | 602/43 |
| 5,885,681 A | | 3/1999 | Korpman | |
| 6,297,420 B1 | * | 10/2001 | Heincke | 602/41 |
| 6,332,570 B2 | * | 12/2001 | Frei | 229/67.1 |

FOREIGN PATENT DOCUMENTS

| | | |
|---|---|---|
| DE | 40007047 | 11/2000 |
| EP | 1138293 A1 | 10/2001 |

* cited by examiner

*Primary Examiner*—Jeanette Chapman

(57) ABSTRACT

The present invention provides an absorbent article having a silhouette that includes a first portion and a second portion, wherein the second portion is in opposite relation to the first portion, and a pair of opposed longitudinally extending sides connecting the first portion to the second portion. The absorbent article also contains a layered portion with a substantially transparent cover layer that absorbs fluid, a substantially transparent backsheet layer, and an optional absorbent core, which may be substantially transparent. At least one flap may optionally extend laterally from a longitudinally extending side.

26 Claims, No Drawings

DISCRETE ABSORBENT ARTICLES

This application is a continuation-in-part of Ser. No. 09/740,337 filed Dec. 19, 2000.

FIELD OF THE INVENTION

This invention relates to an absorbent article, such as pantyliners. More particularly, the present invention relates to discrete pantyliners for use with conventional and thong-type underwear. The invention includes means for attaching the absorbent article to underwear such that the attachment means are not discernible through the clothing of the user.

BACKGROUND OF THE INVENTION

Currently, absorbent articles for sanitary protection, such as, pantyliners, sanitary napkins, and incontinence pads, must fit a variety of individual body shapes and sizes. In particular, women have an almost infinite variety of body shapes and muscle tone in the upper thigh region. A product that offers superior comfort, fit, and protection for one woman may be deficient for another woman due to her body shape and muscle tone.

The availability of different types of underwear also affects the choice of absorbent articles for sanitary protection. For example, conventional pantyliners and napkins are typically designed to be used with underwear having a full sized crotch portion, e.g., briefs and bikinis. However, such conventional pantyliners and napkins attach poorly to underwear having an abbreviated crotch portion, e.g., thong or G-string, which have a substantially narrower posterior end compared to the anterior end. As a result, many women purchase multiple types of sanitary protection depending on the underwear they choose to wear.

One problem with pantyliners, especially those for use with thong underwear, is their ability to be secured to such underwear and to stay in place. For example, there is little surface area of fabric at the narrow posterior end of such pantyliners for such pantyliners to attach. Additionally, the area between the buttocks is sensitive and subject to a high degree of movement.

Attaching a pantyliner to underwear, including thong, often includes at least one flap, tab or wing that extends laterally from a side edge of the liner that wraps around to the outside of the underwear fabric and attaches thereto. As used herein, "flap," "tab," and "wing," whether plural or singular, are interchangeable and shall have the same meaning. Attachment of the flaps is typically accomplished by having an adhesive on the side of the flaps that face the outer underwear fabric.

Typically, absorbent articles used as sanitary protection are white. Because the materials, e.g., fibers and polymers, used to make the components, e.g., cover, absorbent core and barrier, of such absorbent articles often do not have the desired whiteness, pigments, dyes, or color imparting materials, such as, titanium dioxide, are added to such materials to produce the desired whiteness. However, for example, a cover and backsheet produced from such pigmented materials may make the flaps highly visible, thereby reducing discretion.

Accordingly, the need exists for a pantyliner that will attach securely to thong underwear and stay there, so as not to be discernible, especially through clothing. There is also a need for a pantyliner having a conventional silhouette that provides discretion because it is substantially transparent.

SUMMARY OF THE INVENTION

The present invention provides an absorbent article having a silhouette that includes a first portion and a second portion, wherein the second portion is in opposite relation to the first portion, and a pair of opposed longitudinally extending sides connecting the first portion to the second portion. The absorbent article also contains a layered portion with a substantially transparent cover layer that absorbs fluid, a substantially transparent backsheet layer, and an optional absorbent core, which may be substantially transparent. At least one flap may optionally extend laterally from a longitudinally extending side.

DETAILED DESCRIPTION OF THE INVENTION

The absorbent articles of this invention, include, but are not limited to, sanitary napkins, pantyliners, incontinence devices, wound care articles, e.g., surgical dressings and adhesive bandages, shoe liners and the like.

As is well known to those skilled in the art, absorbent articles that are worn externally generally have a layered construction with a body-facing surface that is oriented to face the wearer during use and a garment-facing surface oriented in the opposite direction from the body-facing surface. Typically such articles have a liquid previous cover on the body-facing surface of the article, an absorbent core and a backsheet on the garment-facing surface of the article. The absorbent core is interposed between the cover and the backsheet. The cover and the backsheet encase all components of the article. The cover and the backsheet may be joined or sealed to each other along their peripheral edge using any method known in the art.

Flaps, also known as wings, tabs and the like, are generally flexible and configured to be folded over the edges of the underwear so that the flaps anchor or secure the absorbent article to the underwear.

According to the present invention, the cover and backsheet are made from pigment-free materials. The cover, backsheet or a combination thereof may be used to form flap, thereby creating flaps that are formed from pigment-free materials. In a preferred embodiment, the cover and backsheet are substantially coextensive and are joined together about the periphery of the absorbent article. This results in a periphery, including any flap(s), that is substantially transparent.

As used herein, substantially transparent refers to those materials having a transparency of between about 60 to 100 percent light transmittance. Essential criteria of transparency are total transmittance, haze and clarity. Total transmittance is the ratio of total transmitted light to incident light. It is reduced by reflectance and absorbance. Haze is the percentage is the percentage of transmitted light that deviates from the incident beam by more than about 2.5 degrees on average. Clarity can be evaluated at angles of less than about 2.5 degrees.

In accordance with an embodiment of the present invention, there is provided a novel absorbent article, having a pigment-free body-facing fluid permeable cover sheet, a pigment-free fluid impermeable backsheet, which in the case of sanitary absorbent articles, face the users garment when in use.

In another embodiment of the present invention, there is provided a novel absorbent article, having a pigment-free body-facing fluid permeable cover sheet, a pigment-free fluid impermeable backsheet, which in the case of sanitary absorbent articles, face the users garment when in use, and a pigment-free absorbent core between the cover sheet and the backsheet.

In an alternate embodiment of the present invention, the absorbent article includes at least one flap extending laterally outward that is substantially transparent. The flap being made from the backsheet, the cover, or both.

The pigment-free liquid permeable cover sheet of an absorbent article of the present invention may be formed from any fluid previous material that is comfortable against the skin and permits fluid to penetrate to the absorbent core. The cover should retain little or no fluid in its structure in order to provide a relatively dry surface next to the skin. The cover may be a fibrous fabric made of fibers, including bicomponent fibers, or filaments of polymers, such as polyethylene, polypropylene, polyester, or cellulose. Alternatively, the cover may be formed from an apertured film, plastic nets, webs and the like. Any of these materials may be used provided that the cover, especially the outer edge portion be free of any pigment and be substantially transparent. The cover may be, for example, a 9 gsm polypropylene having code SB-PTE 09 available from Shalag, Upper Tieberias, Israel.

In a preferred embodiment, the cover is a pigment-free, non-woven fabric formed from an interconnected network thermoplastic polymer fibers, at least a portion of the non-woven fabric having a three-dimensional thickness profile.

The optional absorbent core of an absorbent article of the present invention can be a fluffy batt cut from a relatively loose web of non-woven fibers having a relatively high absorptive capacity. While the absorbent core can have any shape or silhouette, it usually has an asymmetric configuration. The absorbent core is usually smaller than the backing sheet and the cover. The absorbent core may also be a fibrous batt having an integral densified layer. In such a case, the absorbent core is positioned on the backing sheet of the absorbent article so that the densified layer adjoins the backing sheet. The densified layer has relatively higher wettability and liquid retentivity than the rest of the aforesaid batt and usually is formed by slightly moistening one surface of the batt and thereafter compressing the moistened surface.

An absorbent core may contain any material that absorbs bodily secretions including, but not limited to pulp, polymeric fibers and filaments, sphagnum moss, natural fibers, superabsorbent polymers (including fibers, particulate material and foams), absorbent foams, and other such absorbent materials. The core may optionally be any substrate, e.g., tissue, woven, nonwoven, netted material, lace, foam, and apertured polymeric film. This substrate may be treated with a treating solution of polyacrylic acid oligomers that are crosslinked onto the substrate via removal of the solvent. Additionally, a platicizing agent, such as, e.g., glycerine, carbowax, PEG 400-900, etc. may be included in the treating solution in an amount of about up to 20%. Such solutions of polyacrylic acid oligomers include, but are limited to, FULLATEX, (code PD-8081H from HB Fuller Co., St. Paul, Minn,), which is a solution having 80% water and 20% polyacrylic acid oligomer. Crosslinking agents that may be used include, but are not limited to, ammonium zirconyl carbonate (available as 5% BACOTE 20 from Magnesium Electron, Flemington, N.J), azirdine (available as NEOC-RYL from Zeneca Resins, Wilmington, Del.). One of the advantages of such treated absorbent cores is that they are more transparent than other cores, e.g., those made of pulp. In addition, such treated cores may become more transparent upon the addition of liquid.

The absorbent core may be formed from cellulosic fibers and superabsorbent polymer particles. The absorbent core may also include additional materials such as odor control material, wetness indicator material, materials for administering or delivering medicaments, such as encapsulated medicaments, and materials for maintaining skin moisture, such as encapsulated moisturizers.

The backsheet of an absorbent article of the present invention may be of any flexible, pigment-free material that prevents the transfer of fluid through it, but does not necessarily prevent the passages of vapors. Backsheets that are previous to vapor are known as breathable backsheets. In general, these backsheets are intended to allow the passage of vapor or water molecules through them while retarding, at least to a degree, the passage of fluid. Monolithic film technology provides materials that can be used to form sheets that allow vapor transmission, but are relatively impervious to liquids. Commonly used materials are segmented block copolymers, polyvinyl alcohol, polyurethane, cellulosics and blends thereof. Other materials that may be used as impermeable barriers may be chosen from films of polypropylene, polyethylene, polyesters, polyamides, polyethylene vinyl acetate, polyvinyl chloride, and polyvinylidene chloride. Co-extruded and laminated to combinations of the foregoing, wherein such combinations are permitted by the chemical and physical properties of the film, may be used. Fluid impermeable nonreticulated foams may also be used. Films that are fluid barriers, but permit vapors to transpire, i.e., "breathable films," may also be used. These include in particular, monolithic, porous or microporous films, as previously described. The vapors most commonly used to demonstrate a film's breathability are water vapor, sometimes referred to as moisture vapor, and oxygen.

A suitable backsheet material can be a pigment-free monolithic film made from segmented block copolymers where one block is hydrophilic and the other block hydrophobic in nature, alternative materials for monolithic films are polyvinyl alcohol, polyurethane, cellulosics and blends thereof In a preferred embodiment, the backsheet is made from a pigment-free and filler-free monolithic sheet made from segmented block copolymers. For example, the back sheet may be 0.8 mil, polypropylene film such as that supplied by the Edison Plastic Co. (Newport News, Va.) (Code XP-766-B), a film from Filmtech. Corp. (Lehigh Valley, Pa.), or it may be a polyethylene film available from Tredegar Film Products (Richmond, Va.) (Code X28480). Suitable monolithic films are marketed by Atochem under the trade name Pebax, and by Du Pont under the trade name Hytrel.

The backsheet may be fixed or otherwise adhered or secured to the surface of the absorbent core overall or in discrete zones of attachment. The backsheet may be adhered to the cover in an overlapping configuration, for example, parallel to the No sides of the absorbent structure, parallel to the bottom of the absorbent article or in a flange seal extending from the sides of the absorbent structure. When the cover and backsheet are adhered to each other in a flange seal, the cover may additionally be wrapped around the flange seal about the cover; or the backsheet may additionally be wrapped around the flange seal about the cover.

The absorbent article may optionally have a multi-layered structure that may additionally contain a pigment-free transfer layer, which is a low density fluid accepting and fluid releasing layer, that is usually located between the cover and the absorbent core. The transfer layer may be made of relatively less hydrophilic materials and structures than is contained in the absorbent core, such as of webs of polypropylene or polyester nonwovens. Transfer layers may also be made of synthetic fibers, such as polyethylene, polypropylene, polylactic acid, polyester, polyacrylonitrile, polyamide, bicomponent, and mixtures thereof Such highloft webs may be bonded with chemical binders or by thermal means such as by through-air bonding.

The layers of the article may be attached or adhered to one another to form a cohesive unit to enhance the article's stability. Such attachment or adherence may be by any known means, including, for example, adhesive, ultrasonics, co-embossing, thermobonding, mechanical bonding, and the like. However, it is preferred that the adhesive is colorless, e.g., a Gardner color of about 3 or less, and does not inhibit the light transmission, vapor transmission, or breathability of the backsheet. In the case of a pantyliner, a pigment-free construction adhesive is preferred to be present between the cover and the absorbent core and also present between the absorbent core and the backsheet. The construction adhesive serves to hold the layers together and to minimize deformation during use. The adhesive can be applied as either a thin porous film or in a random spray, in a controlled spiral pattern, or in any other application pattern. See, for example, U.S. Pat. Nos. 5,462,538; 5,681,305 and 5,885,681.

The absorbent article, in the case of a pantyliner, may be applied to the crotch of underpants by placing the backsheet of the absorbent article against the inside of the crotch of the underpants. Pressure sensitive adhesive that is colorless or pigment-free may be applied to the outer surface backsheet of the absorbent article to help maintain it in place. As used herein, the term "pressure-sensitive adhesive" refers to any pigment-free releasable adhesive having a Gardner color of about 3 or less or releasable tenacious means that does not substantially decrease light transmissibility. Suitable pressure sensitive adhesives include, for example, water-based adhesives such as acrylate adhesives. Alternatively, the adhesive may be a rapid setting thermoplastic "hot melt" rubber adhesive or two-sided adhesive tape.

A paper release strip that has been coated on one side, may be applied to protect the adhesive on the backsheet prior to use. The coating on the release paper, for example, silicone, reduces adherence of the coated side of the release to the backsheet adhesive. The release strip can be formed from any suitable sheet-like material that, when coated, adheres with sufficient tenacity to the adhesive to remain in place prior to use, but can be readily removed when the absorbent article prior to placement on the wearer's underpants.

The absorbent articles of the present invention can be of various shapes and configurations depending on the intended end use, e.g., sanitary protection, including pantyliners and sanitary napkins specifically for use with thong underwear, surgical dressings or wipes, and the like. Additionally, the present absorbent articles can be incorporated into a disposable or limited use garment as an integral part thereof. For example, an absorbent article made according to the present invention can be a part of disposable training pants and similar garments.

The precise shapes of a pantyliner or sanitary napkin of the present invention may vary as desired. For thong-type underwear, the first portion is wider than the second portion. The midsection between the first portion and second portion may be tapered and narrow at a substantially continuous rate. The midsection may also be biconcave in shape or of a narrow, uniform width. In an alternative embodiment, the silhouette of the pantyliner or sanitary napkin may be substantially rectangular, dog bone, or peanut.

At least one flap may be adjacent to the posterior or second portion. Typically there are two flaps. The design of the flaps is not critical. The flaps may be extensions of the backsheet, the cover, or the cover and backsheet adhered or laminated together.

Absorbent articles also within the scope of this invention also include wound care articles such as bandages, including adhesive bandages. Adhesive bandages usually have a backsheet of perforated plastic or of a woven or knit fabric. The backsheet is covered completely or partially on one side with a pressure sensitive adhesive. An absorbent core is placed in the center of and adhered to the adhesive side of the backing material. The absorbent core typically lies between a cover, which contacts the skin and prevents the absorbent from sticking to the wound, and the backsheet.

Alternately, absorbent articles within the scope of this invention also include shoe liners. Shoe liners usually have a non-skid backing and an absorbent.

After the invention has been described in general hereinbefore, the following example is intended to illustrate details of the invention, without thereby limiting it in any matter.

EXAMPLE

Using a Gardner haze gard plus instrument model number 238 013 796K (BYK-Gardner USA, Columbia, Md.), the transparency of the cover and the backsheet laminated together was measured. A flat sample was placed in a round sample holder (approximately 60 mm diameter). Measurements were taken by placing the flat sample in the appropriate measuring ports of the instrument (haze port was used for transmittance and the haze, clarity port was used for clarity). A series of five readings were taken and averaged to obtain final measurement value. Commercial product 1 was a sheet of transparent plastic from a ZIPPIT bag (The Bag Company, Kennesaw, Ga.). Commercial product 2 was a white commercial film, polypropylene 0.7 mil (Huntsmann Packaging, McAlester, Okla.). The invention was made from pigment-free materials, including a cover being made of 18 gsm/pp 6788 (PGI, Neunkirchen, Germany).

TABLE 1

| Sample | Transparency % | Haze % | Clarity % |
| --- | --- | --- | --- |
| Commercial Product 1 | 93.6 | 8.9 | 96.2 |
| Commercial Product 2 | 44.9 | 100 | 1.94 |
| Present Invention | 84.2 | 84.8 | 59.1 |

During the measurement, the narrow angle scattering was less than 2.5%. The wide angle scattering was greater than 2.5%. Total transmittance was calculated as the ratio of the total light transmitted to incident light. Total transmittance is reduced by reflectance and absorbance. The standard deviations for all measurements were less than 1.

The transmittance of light through the prototype of the invention had substantial transparency.

EXAMPLE 2

Three absorbent articles were made and measured as the samples in Example 1. The absorbent articles contained the following components:

TABLE 2

| | Article 1 | Article 2 | Article 3 |
| --- | --- | --- | --- |
| Cover | Tredegar polyolefin | Shalag polyolefin nonwoven (Code | Shalag polyolefin nonwoven (Code |

TABLE 2-continued

| | Article 1 | Article 2 | Article 3 |
|---|---|---|---|
| | apertured film (Code No. X28028) | No. 42949 SB-PTE09) | No. 42949 SB-PTE09) |
| Laminating Adhesive | — | Fuller block co-polymer hot melt HL 1491 (2 mg/in$^2$) | Fuller block co-polymer hot melt HL 1491 (2 mg/in$^2$) |
| Transfer Layer | — | Tredegar polyolefin apertured film (Code No. X28024) | Tredegar polymeric apertured film (Code No. X28024) |
| Absorbent Core | 3M polyolefin film (Code 3567) | Polyester (Libel-tex T-21) treated with 95% Fullatex PD 8081 H + 5% Bacote 20 | Shalag polyolefin nonwoven (Code No 42949 SB-PTE09) treated 95% Fullatex PD 8081 H + 5% Bacote 20 |
| Laminating Adhesive | Fuller block co-polymer hot melt HL 1491 (2 mg/in$^2$) | Fuller block co-polymer hot melt HL 1491 (2 mg/in$^2$) | Fuller block co-polymer hot melt HL 1491 (2 mg/in$^2$) |
| Backsheet | Tredegar polyolefin film (code 28480) | Tredegar polyolefin film (code 28480) | Tredegar polyolefin film (code 28480) |
| Positioning Adhesive | Fuller block co-polymer hot melt HL 1417 (12 mg/in$^2$) | Fuller block co-polymer hot melt HL 1417 (12 mg/in$^2$) | Fuller block co-polymer hot melt HL 1417 (12 mg/in$^2$) |

Using a Gardner haze gard plus instrument model number 238 013 796K YK-Gardner USA, Columbia, Md.), the transparency of the above absorbent articles were measured. Measurements were taken from a flat sample cut from the center of each article and placed in a round sample holder (about 60 mm diameter). The section measured included all layers of set for the above. The flat sample was placed in the appropriate measuring ports of the instrument (haze port was used for transmittance and the haze, clarity port was used for clarity). A series of five readings were taken and averaged to obtain final measurement value.

| Article No. | Light Transmittance % | Haze % | Clarity % |
|---|---|---|---|
| 1 | 74.6 | 96.3 | 6.66 |
| 2 | 63.8 | 100 | 4.32 |
| 3 | 71.8 | 99.5 | 4.16 |

What is claimed is:

1. An absorbent article comprising:
   (a) a silhouette comprising
      (i) a first portion,
      (ii) a second portion, the second portion being in opposite relation to the first portion, and
      (iii) a pair of opposed longitudinally extending sides connecting the first portion to the second portion; and
   (b) a layered portion comprising;
      (i) a substantially transparent cover layer that absorbs fluid and
      (ii) a substantially transparent backsheet layer.

2. An absorbent article of claim 1, further comprising a substantially transparent absorbent core.

3. An absorbent article of claim 2, wherein the absorbent core is treated with a solution of polyacrylic acid oligomers that are crosslinked in situ upon the removal of solvent onto the absorbent core using a crosslinking agent.

4. An absorbent core of claim 3, wherein the solution of polyacrylic acid oligomers further comprise a plasticizer.

5. An absorbent article of claim 2, further comprising at least one flap laterally extending from the first longitudinally extending side.

6. An absorbent article of claim 5, wherein the flap is substantially transparent.

7. An absorbent article of claim 2, wherein the distance between the pair of longitudinally extending sides decrease from the first portion to the second portion.

8. An absorbent article of claim 7, further comprising at least one flap laterally extending from the first longitudinally extending side.

9. An absorbent article of claim 8, wherein the flap is substantially transparent.

10. An absorbent article of claim 8, wherein the flap is adjacent to the second portion.

11. An absorbent article of claim 2, further comprising an additional flap, wherein the additional flap extends from the opposite longitudinally extending side from the first flap.

12. An absorbent article of claim 11, wherein the flap is substantially transparent.

13. An absorbent article of claim 11, wherein the flap is adjacent to the second portion.

14. An absorbent article of claim 1, further comprising an absorbent core.

15. An absorbent article comprising:
   (a) a silhouette comprising
      (i) a first portion,
      (ii) a second portion, the second portion being in opposite relation to the first portion, and
      (iii) a pair of opposed longitudinally extending sides connecting the first portion to the second portion; and
   (b) a layered portion comprising;
      (i) a substantially transparent cover layer that absorbs fluid,
      (ii) a substantially transparent backsheet layer, and
      (iii) a substantially transparent absorbent core.

16. An absorbent article of claim 15, wherein the absorbent core becomes more transparent upon the addition of water thereto.

17. An absorbent article of claim 15, further comprising at least one flap laterally extending from the first longitudinally extending side.

18. An absorbent article of claim 17, wherein the flap is substantially transparent.

19. An absorbent article of claim 15, wherein the distance between the pair of longitudinally extending sides decrease from the first portion to the second portion.

20. An absorbent article of claim 19, further comprising at least one flap laterally extending from the first longitudinally extending side.

21. An absorbent article of claim 20, wherein the flap is substantially transparent.

22. An absorbent article of claim 21, wherein the flap is adjacent to the second portion.

23. An absorbent article of claim 15, further comprising an additional flap, wherein the additional flap extends from the opposite longitudinally extending side from the first flap.

24. An absorbent article of claim 23, wherein the flap is substantially transparent.

25. An absorbent article of claim 24, wherein the flap is adjacent to the second portion.

26. An absorbent article of claim 1, wherein the absorbent article is selected from the group consisting of a pantyliner, a sanitary napkin, an adhesive bandage, and a shoe liner.

* * * * *